United States Patent
Bennett et al.

[11] 4,001,403
[45] Jan. 4, 1977

[54] METHOD FOR REDUCING THE REPRODUCTIVE FUNCTION OF MAMMALS

[75] Inventors: Donald R. Bennett, Midland, Mich.; James A. McHard, Gainesville, Fla.

[73] Assignee: Dow Corning Corporation, Midland, Mich.

[22] Filed: Mar. 16, 1973

[21] Appl. No.: 342,227

Related U.S. Application Data

[63] Continuation-in-part of Ser. No. 743,602, July 10, 1968, abandoned.

[52] U.S. Cl. .......................... 424/184; 424/DIG. 12
[51] Int. Cl.² ...................................... A61K 31/695
[58] Field of Search ................... 424/184, DIG. 12; 260/448.2

[56] References Cited
UNITED STATES PATENTS

| | | | |
|---|---|---|---|
| 2,911,427 | 11/1959 | Brown | 260/448.2 |
| 2,915,544 | 12/1959 | Holbrook et al. | 260/448.2 |
| 2,961,425 | 11/1960 | Pierce et al. | 260/448.2 |
| 2,979,519 | 4/1961 | Pierce et al. | 260/448.2 |
| 3,070,617 | 12/1962 | Holbrook | 260/448.2 |

OTHER PUBLICATIONS
Borkove, A., "Advances in Pest Control Research," vol. VII (1966) pp. 1–4, 61–63.

*Primary Examiner*—V. D. Turner
*Attorney, Agent, or Firm*—Norman E. Lewis

[57] ABSTRACT

A method for altering the reproductive function of mammals by administering a pharmacologically effective amount of certain fluoroalkyl-substituted organosilicon compounds. As a means of illustration, one can orally or parenterally administer from 1.0 mg. to 100 mg. per kilogram of body weight (either as a single dose or as a daily dosage over a period of time) of an organosilicon compound of the formula

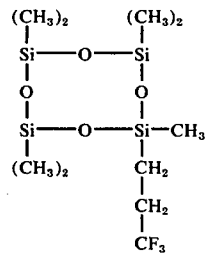

thereby rendering the subject (either a male or female mammal) infertile.

9 Claims, No Drawings

METHOD FOR REDUCING THE REPRODUCTIVE FUNCTION OF MAMMALS

This application is a continuation-in-part of U.S. application, Ser. No. 743,602, filed July 10, 1968 now abandoned.

This invention relates to a method for altering the reproductive function of mammals.

We have discovered that the administration of a pharmacologically effective amount of certain fluoroalkyl-substituted organosilicon compounds can reduce the reproductive function of mammals. More precisely, a male mammal so treated exhibits androgen depressant effects. For example, the sex accessory organs of the male (seminal vesicle, prostate) can be reduced in function and/or size and with sufficient dosage, the male can also be rendered infertile as a result of depression of testes size and function. A female mammal so treated exhibits an alteration of fertility, i.e., the female mammal's capability to conceive is inhibited such that the female may be rendered infertile or abort if pregnant.

The principal object of this invention is to provide therapeutically effective fluoroalkyl-substituted organosilicon compounds which can render a male or female mammal infertile. Another principal object of this invention is to provide a method of administering certain organosilicon compounds which can be useful in the treatment of prostatic hypertrophy by depressing androgen function in males. It is still another object of this invention to provide a method of administering certain organosilicon compounds to females whereby the female's capability to conceive or support and carry a living fetus through a normal pregnancy to a healthy birth can be inhibited. These and other objects will be apparent to one skilled in the art upon reading the detailed description which follows.

In accordance with the present invention there is provided a method for reducing the reproductive function of mammals which comprises administering a pharmacologically effective amount of certain fluoroalkyl-substituted organosilicon compounds to a mammal, the fluoroalkylsilicon compounds being selected from the group consisting of (1) $Si(CH_2CH_2CF_3)_4$,

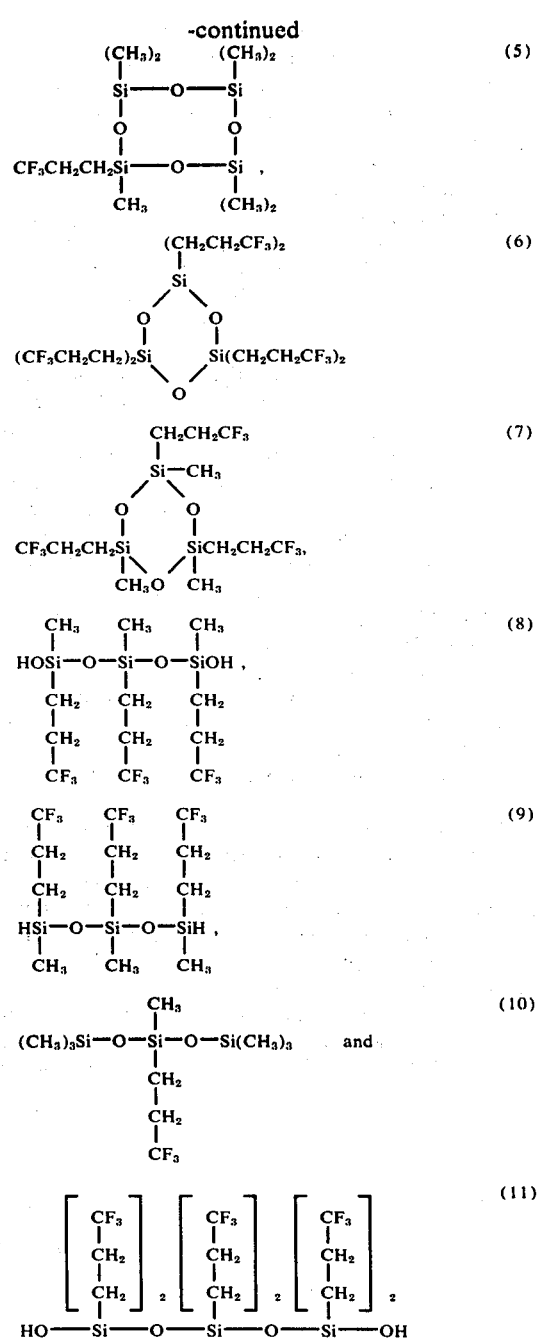

The fluoroalkylsilicon compounds noted herein can be readily prepared by well known techniques described in the literature, e.g., by the cohydrolysis of chlorosilanes or by a suitable Grignard reaction. Specific examples of the preparation of certain of the compounds are found in U.S. Pat. Nos. 2,961,425, 2,915,544, 2,979,519, 2,911,427, 3,070,617 and Canadian Pat. No. 586,889 and 586,917.

The process of the present invention is operative on any mammal, e.g., rodents such as mice, rabbits and rats; domestic animals such as cats, swine, dogs, cattle, horses, and sheep; animals wild in nature such as deer, fox, wolves and lynx; and primates such as monkeys and man.

One can administer the described fluoroalkylsilicon in any pharmacologically acceptable manner. They can be orally administered, parenterally administered or in certain species topically administered. The parenteral mode of administration would of course, include subcutaneous administration, intramuscular administration and the like.

It is of importance to note that the organosilicon compounds described herein can be administered either in pure form in or combination with a pharmaceutically acceptable oral or injectable carrier. Suitable carriers include sesame oil, corn oil, mineral oil and other well known fat soluble carriers commonly employed in numerous pharmaceutical preparations.

As mentioned herein, the dose range of the organosilicon compound is in a pharmacologically effective amount. A dose range of from about 1.0 mg. to about 100 mg. per kilogram of body weight has been found to be suitable; however, the precise dosage is ultimately dependent upon the particular compound and its isomers, the mammal used, the vehicle used, the route of administration, and the specific effects one wishes to achieve. The organosilicon compound may be administered as a single dose or it may be administered in daily dosage over varying periods of time, e.g., from about 7 to about 30 days or more.

The time required to achieve the desired effect is also variable, ranging anywhere from days to weeks or months, depending upon various factors, e.g., the species of mammal, dosage, route of administration, and the degree to which one wishes to reduce the reproductive function.

The particular alteration of reproductive functions which have been observed after administering the compounds of the present invention to male mammals are a decrease in sex accessory organ function (decreased seminal fluid) and size (decreased seminal vesicle) and a decrease in prostatic or testicular function (decreased sperm count) or size.

In view of the above, the method of this invention can be useful for decreasing the size of male sex accessory organs. In this regard, sex accessory organs are more sensitive than the testes to these certain organosilicon compounds so that it is possible to decrease prostatic function and size without producing a significant effect on testicular size. Thus, the method of this invention can be particularly useful for the treatment of prostatic hypertrophy.

If a high dosage level is maintained over a fairly long period of time in females prior to, during and/or following copulation, the anticipated embryo may fail to form or it may be resorbed by the female mammal. It is also possible to prevent pregnancy (contraception) or abort pregnancy in female mammals because of an estrogenic activity of certain of the organosilicon compounds described herein.

In all of the foregoing cases, the pharmacological actions are reversible.

The following examples are illustrative only and should not be construed as limiting the invention which is properly delineated in the appended claims.

EXAMPLE 1

To demonstrate a reduction in the reproductive function, various dosages of fluoroalkyl-substituted organosilicon compounds were administered via gastric intubation to groups of ten male rats (Sprague-Dawley strain). All compounds were administered once daily in a constant volume of 2.0 ml. of sesame oil per kg. of animal body weight for a period of seven days, with autopsy on day eight. Final body weights were determined in the fasted state just prior to sacrifice. A control group of 10 male rats received the same daily dosage of sesame oil only for the 7 day period. The data in Table I shows the results of administering the defined compounds at the specified dose levels. In the table the three numbers in sequence following a particular compound at any given dosage denotes the percent of control value for seminal fluid, seminal vesicle and prostate respectively after conversion of a ratio of the fluid or organ weight to final body weight. Underlined numbers denote statistically significant differences from control values where $p \leq .05$.

TABLE I

RELATIONSHIP OF CHEMICAL STRUCTURE TO AMOUNT OF REDUCTION IN REPRODUCTIVE FUNCTION

| Fluoroalkyl-Substituted Organosilicon Compound | Daily Dosage mg. compound/kg. animal body weight | | | |
|---|---|---|---|---|
| | 100 | 33 | 20 | 10 |
| $CF_3CH_2CH_2Si(CH_3)_2-O-Si(CH_3)_2CH_2CH_2CF_3$ | | | 78 93 96 | |
| $[CF_3CH_2CH_2Si(CH_3)O-]_3$ | | 11 60 * | | 71 95 87 |
| $HO-Si(CH_3)(CH_2CH_2CF_3)-O-Si(CH_3)(CH_2CH_2CF_3)-O-Si(CH_3)(CH_2CH_2CF_3)-OH$ | | 52 69* | | 83 94 86 |

TABLE I-continued

RELATIONSHIP OF CHEMICAL STRUCTURE TO AMOUNT OF REDUCTION IN REPRODUCTIVE FUNCTION

| Fluoroalkyl-Substituted Organosilicon Compound | Daily Dosage mg. compound/kg. animal body weight | | | |
|---|---|---|---|---|
| | 100 | 33 | 20 | 10 |
| $CH_3$   $CH_3$   $CH_3$<br>$\|$      $\|$      $\|$<br>H—Si—O—Si—O—Si—H<br>$\|$      $\|$      $\|$<br>$CH_2$  $CH_2$  $CH_2$<br>$\|$      $\|$      $\|$<br>$CH_2$  $CH_2$  $CH_2$<br>$\|$      $\|$      $\|$<br>$CF_3$  $CF_3$  $CF_3$ | <u>55</u> <u>70</u> <u>69</u> | | <u>78</u> <u>89</u> 100 | |
| $(CH_3)_2$ $(CH_3)_2$<br>$\|$      $\|$<br>Si—O—Si<br>$\|$      $\|$<br>O      O<br>$\|$      $\|$<br>$CF_3CH_2CH_2$—Si—O—Si<br>$\|$      $\|$<br>$CH_3$  $(CH_3)_2$ | <u>65</u> <u>80</u> <u>83</u> | 97 83 <u>89</u> | | |
|                $CH_3$   $CH_3$<br>               $\|$      $\|$<br>$(CH_3)_3Si$—O—Si—O—Si—$OSi(CH_3)_3$<br>               $\|$      $\|$<br>               $CH_2$  $CH_2$<br>               $\|$      $\|$<br>               $CH_2$  $CH_2$<br>               $\|$      $\|$<br>               $CF_3$   $CF_3$ | ** | | | |

\* prostate weight not obtained.
\*\* no significant difference in any of the values from those of the control.

These data demonstrate that different compounds exhibit different levels of activity. For example, 3,3,3-trifluoropropylmethylcyclotrisiloxane, has threshold activity at a dosage of less than 10 mg/kg for seven days and is very effective (showing 89% reduction in seminal fluid production) at a dosage of 33 mg/kg. for seven days. Other compounds, such as the cyclic tetramer and hydrogen containing linear trimer, exhibit moderate levels of activity at a dose level of 100 mg/kg. for seven days. Larger doses of the active compounds will result in testicular atrophy and decreased levels of testosterone in the blood.

It will be noted that a closely-related fluoroalkyl-substituted organosilicon compound, a linear tetramer having trimethylsiloxy endblocking units, did not exhibit even threshold activity at the 100 mg/kg. dose level. Comparison with several other related fluoroalkylorganosilicon compounds has shown the criticality of the chemical structure of the compounds of the claimed method to reduction of the reproductive function in animals.

EXAMPLE 2

This example illustrates the structure-activity-relationship between rat androgen-depressant activity and certain fluoroalkylsilicon compounds.

Groups of 10 male rats (Sprague-Dawley strain) were orally dosed with the fluoroalkylsilicon compounds heretofore defined which were diluted in sesame oil. Oral administration was achieved via gastric intubation. The period of dosage ranged from 1 to 7 days at dosage levels of 1.0 to 50 mg. per kilogram of body weight and 50 to 100 mg. per kilogram of body weight. Final body weights were determined in the fasted state just prior to sacrifice. Sacrifice was carried out on day 4, 5, 6, 7 or 8 depending upon the particular dosage regimen. Various organ weights were determined and ratios of the organ weights (grams) to final body weight (grams) were determined for comparison in both control and treated animals.

Table II indicates the structure-activity-relationship referred to above with respect to dosage range for effect. These dosages represent threshold doses for statistically significant reduction of seminal fluid, seminal vesicle, and/or testes weight ratios as compared to control groups of male rats which were subjected to the same particular dosage regimen, with the exception that only sesame oil was used.

TABLE II

STRUCTURE-ACTIVITY-RELATIONSHIP BETWEEN ANDROGEN-DEPRESSANT ACTIVITY AND CERTAIN FLUOROALKYLSILICON COMPOUNDS

| Compound | Daily Dose mg./kg. | Number of Daily Doses | Sacrifice Day Following First Dose |
|---|---|---|---|
| $\text{HO(CH}_3\text{)(CF}_3\text{CH}_2\text{CH}_2\text{)Si-O-Si(CH}_3\text{)(CH}_2\text{CH}_2\text{CF}_3\text{)OH}$ | 10 | 1 | 5 |
| $\text{CF}_3\text{CH}_2\text{CH}_2\text{Si(CH}_3\text{)}_2\text{-O-Si(CH}_3\text{)}_3$ | 20 | 6 | 7 |
| $[\text{HOSi(CF}_3\text{CH}_2\text{CH}_2\text{)}_2\text{-O-Si(CF}_3\text{CH}_2\text{CH}_2\text{)}_2\text{-O-Si(CF}_3\text{CH}_2\text{CH}_2\text{)}_2\text{OH}]$ | 20 | 6 | 7 |
| Cyclic $[\text{Si(CH}_2\text{CH}_2\text{CF}_3\text{)}_2\text{-O}]_3$ | 100 | 6 | 7 |
| $\text{Si(CH}_2\text{CH}_2\text{CF}_3\text{)}_4$ | 100 | 1 | 5 |
| $(\text{CH}_3)_3\text{Si-O-Si(CH}_3\text{)(CH}_2\text{CH}_2\text{CF}_3\text{)-O-Si(CH}_3\text{)}_3$ | 100 | 1 | 5 |

In addition to showing the chemical structure-activity relationship, these data show that a single dose of certain compounds, such as the hydroxy-functional fluoroalkyl-substituted dimer and tetra-(3,3,3-trifluoropropyl) silane, is effective for at least five days after administration of the dosage.

EXAMPLE 3

This example demonstrates the antifertility activity of

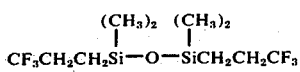

$$\text{CF}_3\text{CH}_2\text{CH}_2\text{Si(CH}_3\text{)}_2-\text{O}-\text{Si(CH}_3\text{)}_2\text{CH}_2\text{CH}_2\text{CF}_3$$

when administered to female rats. The compound was administered orally at a dosage of 33.3 mg/ml. of sesame oil/kg. of body weight/day for 5 days after mating with untreated male rats. Administration, by means of gastric intubation, was begun on the day vaginal sperm were found. This five day dose period then includes the time from insemination to the average time of implantation. A control group of female rats was subjected to the same procedure, except for the omission of the siloxane from the sesame oil. All female rats were sacrificed on day 21 and the number of pregnant females, mean litter size, and mean fetal weight were determined. These data are presented in Table III.

TABLE III

ANTIFERTILITY ACTIVITY IN FEMALE RATS

| | No. Pregnant /No. Mated | Mean Litter Size | Mean Fetal Weight (Grams) |
|---|---|---|---|
| Control (sesame oil only) | 14/14 | 12 | 4.0 |
| $\text{CF}_3\text{CH}_2\text{CH}_2\text{Si(CH}_3\text{)}_2\text{OSi(CH}_3\text{)}_2\text{CH}_2\text{CH}_2\text{CF}_3$ | 2/6 | 13 | 3.9 |

At the 33 mg./kg./day dose level only two of the six females mated were able to conceive. The female's ability to conceive or carry a fetus through a normal pregnancy can be completely inhibited by administration of this particular fluoroalkyl-substituted organosilicon compound at higher dose levels, for example 100 mg./kg./day.

EXAMPLE 4

This example demonstrates the effect on reproductive function of

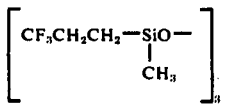

when administered to male mice. The compound was administered to a group of ten male mice (Buckburg strain) orally via gastric intubation at a dosage of 33.3 mg./5 ml. of sesame oil/kg. of body weight/day for 3 days. A control group of ten male mice received the same daily dosage of sesame oil only for the 3 day period. All the mice were sacrificed on the fourth day with final body weights being determined in the fasted state just prior to sacrifice. Upon autopsy the weights of seminal fluid and seminal vesicle were determined and the ratios of organ and fluid weight to final body weight were calculated. The group of mice receiving the fluoroalkylsilicon compound exhibited an 18% reduction in seminal vesicle ratio and a 13% reduction in seminal fluid ratio as compared to the ratios for the control group.

Reasonable modification and variation are within the scope of the invention which is directed to a method of decreasing the reproductive function of male and female mammals.

That which is claimed is:

1. A method for reducing the reproductive function of mammals which comprises administering a pharmacologically effective amount of a certain fluoroalkyl-substituted oganosilicon compound to a mammal, said compound being selected from the group consisting of (1) Si(CH₂CH₂CF₃)₄, Si(CH₂CH₂CF₃)₄,  (1)

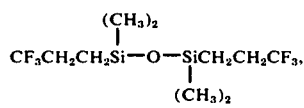  (2)

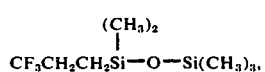  (3)

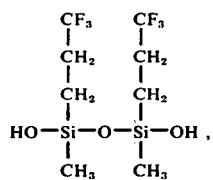  (4)

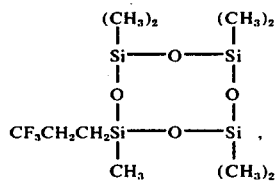  (5)

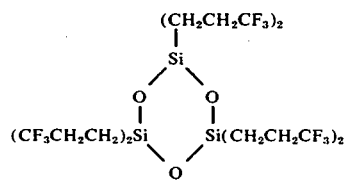  (6)

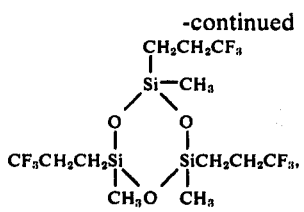  (7)

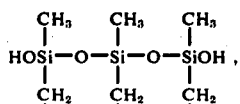  (8)

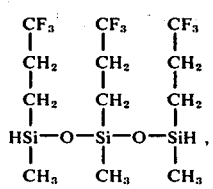  (9)

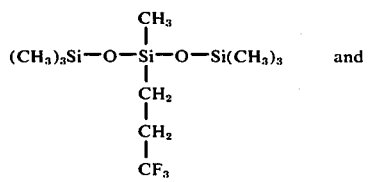  (10) and

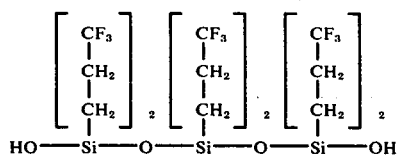  (11)

2. A method in accordance with claim 1 wherein the fluoralkyl-substituted organosilicon compound is administered in an amount in the range of from 1 to 100 mg of compound per kilogram of mammal body weight per day.

3. A method in accordance with claim 1 wherein th fluoroalkyl-substituted organosilicon compound is administered in combination with a pharmaceutically acceptable carrier.

4. A method in accordance with claim 3 wherein the pharmaceutically acceptable carrier is mineral oil.

5. A method in accordance with claim 1 wherein the fluoroalkyl-substituted organosilicon compound is administered to a male mammal.

6. A method in accordance with claim 1 wherein the fluoroalkyl-substituted organosilicon compound is administered to a female mammal.

7. A method in accordance with claim 1 wherein the fluoroalkyl-substituted organosilicon compound is

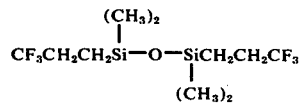

8. A method in accordance with claim 1 wherein the fluoroalkyl-substituted compound is

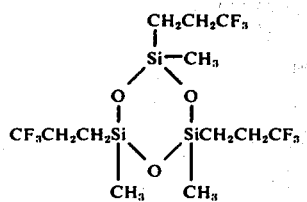
9. A method in accordance with claim 1 wherein
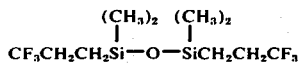
is administered to a female mammal in an amount sufficient to render said female mammal infertile.
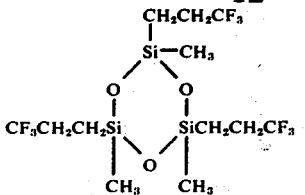
9. A method in accordance with claim 1 wherein
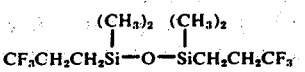
is administered to a female mammal in an amount sufficient to render said female mammal infertile.
* * * * *

UNITED STATES PATENT AND TRADEMARK OFFICE
CERTIFICATE OF CORRECTION

PATENT NO. : 4,001,403
DATED : January 4, 1977
INVENTOR(S) : DONALD R. BENNETT ET AL It is certified that error appears in the above-identified patent and that said Letters Patent are hereby corrected as shown below:

Column 9, Claim 1, delete first line of formula,

--(1) $Si(CH_2CH_2CF_3)_4$,--

Column 12, delete all of Column 12.

Signed and Sealed this

Tenth Day of June 1980

[SEAL]

Attest:

Attesting Officer

SIDNEY A. DIAMOND
Commissioner of Patents and Trademarks